United States Patent [19]

Shibuya et al.

[11] 4,351,947
[45] Sep. 28, 1982

[54] TETRAZOLE DERIVATIVE

[75] Inventors: Chisei Shibuya, Fuji; Masahiro Murakami, Nobeoka; Masateru Kobayashi, Nobeoka; Takanori Sone, Nobeoka, all of Japan

[73] Assignee: Asahi Chemical Industry Co., Ltd., Japan

[21] Appl. No.: 236,542

[22] Filed: Feb. 20, 1981

[30] Foreign Application Priority Data

Mar. 6, 1980 [JP] Japan .................................. 55-27303
Mar. 7, 1980 [JP] Japan .................................. 55-28043

[51] Int. Cl.$^3$ ........................................ C07D 544/036
[52] U.S. Cl. .................................... 548/251; 424/246; 424/269; 544/26
[58] Field of Search ................. 544/16, 27, 26, 28, 544/30; 548/251; 424/269

[56] References Cited

U.S. PATENT DOCUMENTS 3,840,531 10/1974 Greene ........................... 260/243 C
4,110,338 8/1978 Kamiya et al. ..................... 548/251
4,258,195 3/1981 Shibuya et al. ..................... 544/27
4,327,211 4/1982 Murakami et al. ................... 544/27

FOREIGN PATENT DOCUMENTS 49-117487 11/1974 Japan .
49-48559 12/1974 Japan .

OTHER PUBLICATIONS

Wheeler et al., Jour. of Antibiotics, vol. XXXIII, No. 1, pp. 72-75, Jan. 1980.

Primary Examiner—Nicholas S. Rizzo
Attorney, Agent, or Firm—Finnegan, Henderson, Farabow, Garrett & Dunner

[57] ABSTRACT

This invention relates to a tetrazole-5-thiol ester having D-configuration of the formula,

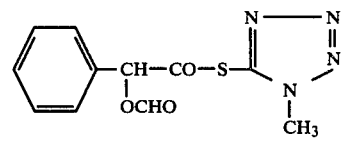

a process for the preparation of the thiol ester and a process for the preparation of cefamandole using the thiol ester.

2 Claims, No Drawings

TETRAZOLE DERIVATIVE

This invention relates to novel tetrazole-5-thiol esters useful as an acylating agent for amines and hydrazines, particularly as active esters for preparing cephalosporin compounds and a process for the preparation of cefamandole using the thiol esters.

Cefamandole is well known as an antibacterial agent and is reported by many documents such as Antimicrobial Agents & Chemotherapy 1(3) 221–234 (1972) by Wick et al., U.S. Pat. No. 3,641,021 Example 4 by Ryan, French Pat. No. 7,310,112 by Greene and U.S. Pat. No. 3,796,801 Example 1 by Guarini. However, the process for preparing the cefamandole in a short reaction time with a higher yield and without causing side reactions has not been reported yet.

An object of this invention is to provide a novel tetrazole-5-thiol ester which can be used as a starting material for preparing cefamandole and to provide a method of the production thereof.

Another object of this invention is to provide a method of preparing cefamandole with a higher yield from the tetrazole-5-thiol ester.

Accordingly, the present invention in one embodiment provides a tetrazole-5-thiol ester of the formula:

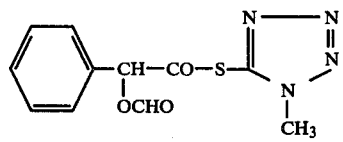

The present invention in another embodiment provides a process for preparing the above described compound of formula (I).

In a further embodiment, the invention provides a process for preparing a compound of the formula:

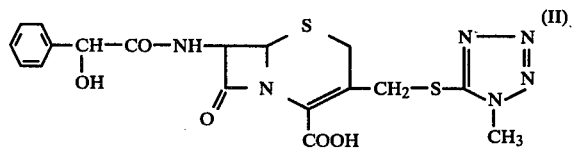

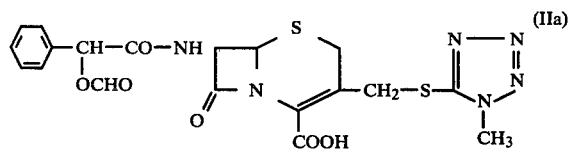

or

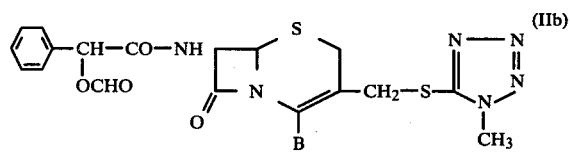

or salts of compounds of formulas (II) and (IIa), respectively, wherein B is a carboxylic acid ester group, which comprises reacting the tetrazole-5-thiol ester of the formula (I) with a compound of the formula (IIIa):

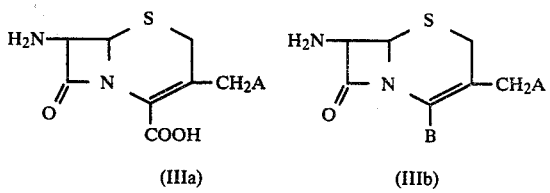

or its salt or with a compound of the formula (IIIb) wherein A is an acetoxy group, a benzimidazol-2-ylthio group or a 1-methyl-1H-tetrazol-5-ylthio group, and B has the same meaning as above.

The tetrazole-5-thiol ester of the formula (I) of this invention is O-formyl-D-(—)-mandeloyl-1-methyl-1H-tetrazol-5-ylthiol ester.

The compound of formula (I) of this invention is novel compound and useful as the sleep-inducing agent and the antibacterial agent of high value.

More specifically, the compound of formula (I) of this invention has been found to exhibit an anesthetic effect, i.e., a sleep-inducing effect according to the following experiment.

Male ddY-strain mice aged 7 or 6 weeks, each group consisting of 8 animals, were given an intravenous injection of 35 mg/kg of sodium thiopental in an amount corresponding to a certain anesthetic period of time, the period of loss of the righting reflex being measured as the anesthetic effect. As a test drug, O-formyl-D-(—)-mandelic acid 1-methyl-1H-tetrazol-5-ylthiol ester was dissolved in dimethyl sulfoxide and the test drug thus prepared was orally administered to the animals at a rate of 0.05 ml/10 g weight one hour before the administration of sodium thiopental. The results are shown in the Table below.

TABLE

| Compound | Amount of Administration (P.O.) (mg/kg) | Period of Time of Anesthesia (Average Value) (minutes) |
|---|---|---|
| O-formyl-D-(—)-mandelic acid 1-methyl-1H-tetrazole-5-ylthiol ester | 400 | 32.5 |
| O-formyl-D-(—)-mandelic acid 1-methyl-1H-tetrazole-5-ylthiol ester | 200 | 20.6 |
| O-formyl-D-(—)-mandelic acid 1-methyl-1H-tetrazole-5-ylthiol ester | 100 | 9.8 |
| Comparative Group | 0 | 8.7 |

As is clearly to be seen from the Table as described above, the period of time of anesthesia of O-formyl-D-(—)-mandelic acid 1-methyl-1H-tetrazol-5-ylthiol ester used in an amount of 400 mg/kg is 3.73 times greater than that of the comparative group. Thus, the prolongation effect on the period of time of anesthesia according to the compound of formula (I) of this invention is remarkable.

Also, O-formyl-D-(—)-mandelic acid 1-methyl-1H-tetrazol-5-ylthiol ester of this invention had a minimum inhibitory concentration of 50 μg/ml to *Cornynebacterium diphtheriae* P.W. 8 and therefore possesses an antibacterial activity.

Also, the compund of the formula (I) of this invention is useful as the acylating agent for amines and hydrazines, particularly as the active ester for preparing cephalosporin compounds.

The tetrazole-5-thiol ester of the formula (I) of this invention can be prepared by reacting a 1-methyl-1H-tetrazole-5-thiol or its derivative with a free carboxylic acid of O-formyl-D-(−)-mandelic acid or a reactive derivative of the carboxylic group in the O-formyl-D-(−)-mandelic acid optionally in a solvent.

The derivatives of the 1-methyl-1H-tetrazole-5-thiol which can be employed in this invention include the salts of sodium and potassium; the reaction products of trimethylaluminum and triethylaluminum; the trimethylsilyl derivative and the triethylsilyl derivative; and the trifluoracetates.

When the free carboxylic acid of O-formyl-D-(−)-mandelic acid is used in this invention, a dehydrating agent for condensation is added to the reaction system. The dehydrating agents for condensation which can be employed in this invention include the conventional agents used in this field such as N,N'-dicyclohexylcarbodiimide, N,N'-diisopropylcarbodiimide, carbonyldiimidazol and N-cyclohexyl-N'-morpholinoethylcarbodiimide. Generally, the amount of the dehydrating agent is 0.5 to 10 moles and preferably 1 to 5 moles per mole free carboxylic acid, amounts outside these ranges are possible depending on the system selected.

When the reactive derivative of the carboxylic group is used, it is unnecessary to employ the dehydrating agent for condensation.

The reactive derivatives of the carboxylic group in the O-formyl-D-(−)-mandelic acid which can be employed in this invention include the acid halides, the esters, the mixed acid anhydrides, the acid amides, the acid azides and the nitriles.

Specific examples of suitable derivatives include the acid chloride; the mixed acid anhydrides of a dialkylphosphoric acid; the mixed acid anhydrides of a phenylphosphoric acid; the mixed acid anhydride of a diphenylphosphoric acid, the mixed acid anhydride of a dibenzylphosphoric acid; the mixed acid anhydride of halogenated phosphoric acids such as chlorophosphoric and bromophosphoric acid; the mixed acid anhydride of a dialkylphosphorous acid; the mixed acid anhydride of sulfurous acid; the mixed acid anhydride of thiosulfuric acid; the mixed acid anhydride of sulfuric acid; the mixed acid anhydride of an alkylcarbonic acid; the mixed acid anhydride of an aliphatic carboxylic acid such as pivalic acid, pentanoic acid, isopentanoic acid, 2-ethylbutanoic acid, trichloroacetic acid and trifluoroacetic acid; the mixed acid anhydride of an aromatic carboxylic acid such as benzoic acid; the symmetric acid anhydrides; the acid amides of imidazole, a 4-substituted imidazole, dimethylpyrazole, triazole, tetrazole, ammonia, methylamine and dimethylamine; the esters such as methyl ester, ethyl ester, cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl ester, phenylthioester, p-nitrophenylthioester, 2,4-dinitrophenylthioester, p-cresylthioester, carboxymethylthioester, pyranyl ester, pyridyl ester, 8-quinolylthioester, the ester of N,N-dimethylhydroxylamine, 1-hydroxy-2-(1H)-pyridone, N-hydroxysuccinimide or N-hydroxyphthalimide.

The 1-methyl-1H-tetrazole-5-thiol or its derivative is dissolved or suspended in a solvent and the solution or the suspension is added with the carboxylic acid, the reactive derivative of the carboxylic group or solution or suspension thereof. As a general rule the reaction is carried out for about 30 minutes to about 24 hours. Reaction times outside this range are possible depending on the system selected.

Any solvent which is inert to the reactants and can dissolve or suspend the reactants can be employed in this invention.

Specific examples of suitable solvents include dioxane, ethyl acetate, methylene chloride, chloroform, hexane and aqueous solutions of sodium hydroxide or potassium hydroxide.

The reaction temperature which can be employed in the preparation of the tetrazole-5-thiol ester of the formula (I) may be varied within a wide range of temperatures. In general, the reaction temperature is about −20° C. to about 50° C., and preferably 0° C. to about 50° C. Reaction temperatures outside this range are possible depending on the system selected.

In general 0.5 to 2.0 moles and preferably 0.9 to 1.2 moles of the thiol or its derivatives are reacted with 1 mole O-formyl-D-(−)-mandelic acid or its derivative. Other ratios are possible depending on the system selected. After the reaction is completed, the desired compound of 1-methyl-1H-tetrazole-5-thiol ester or its derivative of the formula (I) can be recovered from the reaction mixture and purified by the conventional techniques. For example, the solvent is evaporated from the reaction mixture and the crude product thus obtained is washed, dried or recrystallized.

Since the 1-methyl-1H-tetrazole-5-thiol ester or its derivative of the formula (I) has a very active thiol ester group

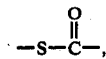

the compound can easily acylate amines, hydrazines, phenols or alcohols with a high yield.

The purification of this acylation product is very simple and this is a remarkable aspect of the invention. When the compound of the formula (I) of this invention is used as an acylating agent, 1-methyl-1H-tetrazole-5-thiol is precipitated with the proceeding of acylation. Accordingly, the product can be easily separated from the reaction mixture and purified. Further, as the 1-methyl-1H-tetrazole-5-thiol is amphoteric, it can be easily removed by washing with either aqueous solution of acid and alkali. Although the 1-methyl-1H-tetrazole-5-thiol might remain in the product, it can be easily removed by the above described washing. Accordingly, by using the compound of the formula (I) of this invention as an acylating agent, acylated compounds having high purity can be easily obtained.

The O-formyl-cefamandole having D-configuration in the side chain of the formula (IIa) of this invention can be prepared by reacting 1-methyl-1H-tetrazole-5-thiol ester or its derivative of the formula (I) with the compound of the formula:

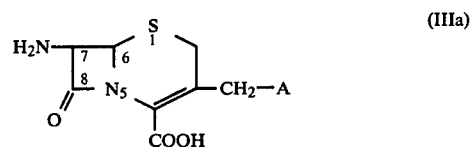

(IIIa)

wherein A is an acetoxy group, a benzimidazol-2-ylthio group or a 1-methyl-1H-tetrazol-5-ylthio group; or its salt; or its ester of the formula (IIIb):

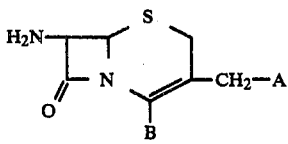
(IIIb)

wherein A is the same as defined above and B is a carboxylic acid ester group.

Suitable examples of the derivatives of the compound (IIIa) and (IIIb) which can be employed in this invention include the salts of alkali metals such as sodium and potassium; the salts of alkaline earth metals such as calcium and magnesium; the salts of nitrogen-containing organic bases such as trimethylamine, triethylamine, pyridine, N-methylpiperidine and N-methylmorpholine; and the esters (where the carboxylic acid group carries a usual protective group) which can be easily converted into the compound of the formula (IIIa) or its salt, for example, by catalytic reduction, chemical reduction, or hydrolysis, released by catalytic reduction, chemical reduction or under other mild conditions.

The preparation of the O-formyl-cefamandole of the formula (IIa) is generally conducted in a solvent. Any solvents which are inert to the reactants can be employed in this invention.

Specific examples of suitable solvents used include water, acetone, dioxane, acetonitrile, toluene, chloroform, methylene chloride, ethylene chloride, tetrahydrofuran, ethyl acetate, formic acid, pyridine, trifluoroacetic acid, N,N-dimethylformamide, methanol, ethanol, methoxy ethanol, diethyl ether, isopropyl ether, dimethyl sulfoxide and any mixtures of water with the above described organic solvents.

In general the temperature of the above described reaction which can be employed in this invention is about −50° C. to about 100° C., and preferably about 0° C. to about 80° C. The period of time of the above described reaction typically ranges from about 10 minutes to several tens of hours, and preferably from about 0.5 hour to about 6 hours. However, reaction temperatures and times outside the ranges given are possible depending on the system selected. The above described reaction is continued until the compounds of the formulae (IIa) and (IIb) are produced in a most appropriate amount.

Further, in the above described reaction an acid catalyst can be employed, if necessary. Specific examples of the acid catalysts which can be employed in this invention include inorganic acids such as hydrochloric acid and sulfuric acid; sulfonic acids such as paratoluenesulfonic acid and methanesulfonic acid; organic acids such as aliphatic carboxylic acids like propionic acid, and such as 1-methyl-1H-tetrazolyle-5-thiol. The inorganic acid and the thiol are preferred from the viewpoint of high yield and short reaction period.

The amount of the catalyst which can be employed is not specifically limited; however, generally, 0.01 to 0.1 mole per mole of the compound of the formula (IIIa) or (IIIb) are used and preferably 0.05 mole per mole of 7-amino-3-(benzimidazol-2-ylthiomethyl)-3-cephem-4-carboxylic acid.

In case of compounds of the formula (IIIa) or (IIIb) especially 7-amino-cephalosporanic acid or 7-amino-3-(1-methyl-1H-tetrazol-5-ylthiomethyl)-3-cephem-4-carboxylic acid, it is preferred that the reaction between the compound of the formula (I) and the compound of the formula (IIIa) or (IIIb) is conducted at a pH ranging from about 1 to about 10. A more preferred pH is about 2 to about 9.

Generally, the amount of the compound of the formula (I) which can be employed ranges from about 0.5 mole to about 2.0 moles and preferably from about 0.9 mole to about 1.2 moles per mole of the compound of the formula (IIIa) or (IIIb). However, other ratios are possible depending on the selected system.

The reaction product (IIa) or its salt is separated and collected by conventional methods from the reaction mixture. The reaction product (IIb) is further subjected to a cleavage of the ester group, for example, by catalytic reduction, chemical reduction or hydrolysis in order to isolate compound (IIa) or its pharmaceutically acceptable salt.

The O-formyl-cefamandole of the formula (IIa) thus obtained can be converted, by the conventional methods, into the salt of an alkali metal, the salt of ammonium and the salt of an alkaline earth metal.

Further, the O-formyl-cefamandole of the formula (IIa) or its salt can be converted into the cefamandole of the formula (II) by treating the O-formyl-cefamandole or its salt with an alkaline solution such as an aqueous solution of an alkali such as sodium carbonate and sodium bicarbonate.

The following examples are given to illustrate the present invention more specifically. However, it should be understood that the invention is in no way limited by these examples. Room and ambient temperature means about 25° C.

EXAMPLE 1

In 100 ml of anhydrous ethyl acetate were dissolved 2.32 g (0.02 mole) of 1-methyl-1H-tetrazole-5-thiol and to the solution were added 3.6 g (0.02 mole) or O-formyl-D-(−)-mandelic acid. Then to the solution was added 4.1 g (0.02 mole) of N,N'-dicyclohexylcarbodiimide with stirring at 5° C. and the stirring was continued for 2 hours at 5° C. After the solution was left to stand overnight at 0° C., the precipitate thus formed was removed by filtration. The filtrate was washed twice with 90 ml of saturated aqueous sodium chloride solution in each time and dehydrated with magnesium sulfate anhydride, and then ethyl acetate was removed from the dehydrated product at room temperature under reduced pressure to give 5.2 g of an oily compound, i.e., O-formyl-D-(−)-mandelic acid 1-methyl-1H-tetrazol-5-ylthiol ester at a yield of 93%.

Infrared Absorption Spectrum: $\nu_{C=O}$:1740 cm$^{-1}$.

Elemental Analysis Values: Calculated (%) : C, 47.5; H, 3.60; N, 20.1; S, 11.5; Found (%) : C, 47.9; H, 3.65; N, 20.2; S, 11.4.

NMR Spectrum (CDCl$_3$), δ ppm: 3.86 (s, 3H), 6.40 (s, 1H), 7.45 (m, 5H), 8.27 (s, 1H)

EXAMPLE 2

To an aqueous solution consisting of 0.84 g. of sodium hydrogen-carbonate, 1.36 g (0.005 mole) of 7-amino-cephalosporanic acid and 100 ml of water were added at once the solution containing 1.8 g (0.0065 mole) of O-formyl-D-(−)-mandelic acid-1-methyl-1H-tetrazol-5-ylthiol ester obtained in the above described Example 1 and 10 ml of acetone at room temperature. Then the solution was stirred at 50° C. to 55° C. for 3 hours. The reaction solution was washed with ether and was added with 3N hydrochloric acid to adjust the pH of the solution to 3, and then the solution was extracted twice with 100 ml of ethyl acetate in each time. The layer of ethyl acetate was washed with saturated aqueous sodium chloride solution. After the layer was dehydrated with anhydrous magnesium sulfate the ethyl acetate was evaporated and the residue dried. The residue thus obtained was pulverized by adding ether thereto to give powdery solid. The solid was filtered and was washed with ether and then dried to give 2.0 g of 7-(D-2-formyloxy-2-phenylacetoamide)-3-(1-methyl-1H-tetrazol-5-ylthiomethyl)-3-cephem-4-carboxylic acid (O-formylcefamandole) at a yield of 81%.

Elemental Analysis Values: Calculated (%) : C, 46.5; H, 3.67; N, 17.1; S, 13.1; Found (%) : C, 46.7; H, 3.75; N, 17.0; S, 13.0.

NMR Spectrum (DMSO-$d_6$), δ ppm: 3.52 (s, 2H), 3.88 (s, 3H), 4.10 (s, 2H), 4.92 (d, 1H); 5.62 (q, 1H), 6.06 (s, 1H), 7.26 (s, 1H), 8.28 (s, 1H).

EXAMPLE 3

The solution consisting of 1.8 g (0.005 mole) of 7-amino-3-(benzimidazol-2-ylthiomethyl)-3-cephem-4-carboxylic acid, 50 ml of N,N-dimethylformamide and 50 ml of water was heated at 60° C. and to the solution was added 1.8 g (0.065 mole) of O-formyl-D-(—)-mandelic acid-1-methyltetrazol-5-ylthiol ester. Further, the solution was added with 5 ml of 0.5N hydrochloric acid and stirred at 60° C. for 3 hours. The reaction solution was washed with ether and then added with 1N hydrochloric acid to adjust the pH of the solution to 1.5. The obtained solution was extracted three times with 100 ml of ethyl acetate in each time. The layer of ethyl acetate was washed with saturated aqueous sodium chloride solution. After the layer was dehydrated with anhydrous magnesium sulfate the ethyl acetate was evaporated and the residue dried. The residue thus obtained was pulverized by adding ether thereto to give powdery solid. The solid was filtered and was washed with ether and then dried to give 2.1 g of 7-(D-2-formyloxy-2-phenylacetoamide)-3-(1-methyl-1H-tetrazol-5-ylthiomethyl)-3-cephem-4-carboxylic acid at a yield of 85%. The analytical values were identical with those of Example 2.

EXAMPLE 4

The solution consisting of 3.1 g (0.011 mole) of O-formyl-D-(—)-mandelic acid-1-methyl-1H-tetrazol-5-ylthiol ester and 20 ml of tetrahydrofuran (THF) was cooled at 5° C., and was added to 30 ml of 50% aqueous tetrahydrofuran solution containing 3.3 g (0.01 mole) of 7-amino-3-(1-methyl-1H-tetrazol-5-ylthiomethyl)-3-cephem-4-carboxylic acid and 1 g (0.01 mole) of triethylamine while the temperature of the solution was maintained at 5° C. with stirring. The solution was further stirred at room temperature for 4 hours. Then the THF was removed from the solution under reduced pressure and the solution was extracted twice with 25 ml of ethyl acetate in each time. After the extract was washed with 10 ml of saturated aqueous sodium hydrogencarbonate solution, the extract was added to the water layer separated at the extraction as described above. To the solution was added 6N hydrochloric acid to adjust the pH of the solution to 2.5, and the solution was extracted three times with 50 ml of ethyl acetate in each time. The ethyl acetate layer was washed with 15 ml of water and dehydrated with anhydrous magnesium sulfate and then ethyl acetate was evaporated and the residue dried to give 4.4 g of 7-(D-2-formyloxy-2-phenylacetoamido)-3-(1-methyl-1H-tetrazol-5-ylthiomethyl)-3-cephem-4-carboxylic acid at the yield of 90%.

In 40 ml of water containing 3.2 g of sodium carbonate were dissolved 3.5 g of 7-(D-2-formyloxy-2-phenylacetoamido)-3-(1-methyl-1H-tetrazol-5-ylthiomethyl)-3-cephem-4-carboxylic acid thus obtained, and the solution was stirred at room temperature for 3 hours. Then the solution was diluted with 20 ml mixture of ice and water and added with 6N hydrochloric acid to adjust the pH of the solution to 2.5, and was extracted three times with 50 ml of ethyl acetate in each time. The layer of ethyl acetate was washed twice with 20 ml of water in each time and dehydrated with anhydrous magnesium sulfate, and then ethyl acetate was evaporated and the residue dried to give 7-D-mandelamido-3-(1-methyl-1H-tetrazol-5-ylthiomethyl)-3-cephem-4-carboxylic acid (cefamandole) in the form of yellow foam.

NMR Spectrum (D$_2$O), δ ppm: 3.50 (s, 2H), 3.92 (s, 3H), 4.20 (s, 2H), 5.04 (d, 1H), 5.24 (s, 1H), 5.64 (d, 1H), 7.44 (s, 5H).

Thus obtained 7-D-mandelamido-3-(1-methyl-1H-tetrazol-5-ylthiomethyl)-3-cephem-4-carboxylic acid (cefamandole) was dissolved in 50 ml of anhydrous ethanol and the solution was filtered. To the filtrate was added dropwise 6 ml of absolute methanol containing 1.09 g (0.008 mole) of sodium acetate trihydrates with stirring to give sodium cefamandole in the form of condensed slurry. The slurry was stirred at 0° C. to 5° C. for 30 minutes. The sodium cepfamandole was collected by filtration and washed with ethanol and then dried in vacuum to give 2.4 g of the compound at the yield of 51%.

Melting Point: 133°–135° C.

Ultraviolet Spectrum (Phosphoric acid buffer solution of pH 6.4): λ max = 269 mμ.

What is claimed is:

1. A tetrazole-5-thiol ester having D-configuration of the formula:

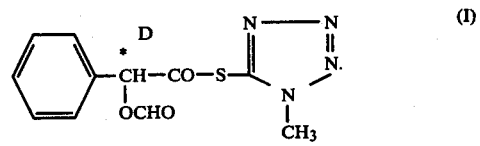

2. A process for preparing the tetrazole-5-thiol ester of claim 1, which comprises reacting (1) a 1-methyl-1H-tetrazole-5-thiol, (2) its sodium or potassium salts, (3) its reaction products of trimethylaluminum or triethylaluminum, (4) its trimethylsilyl derivative and the triethylsilyl derivative or (5) its trifluoroacetates with (1) O-formyl-D-—)-mandelic acid (in the presence of a dehydrating agent in case of a reaction with 1-methyl-1H-tetrazole-5-thiol), (2) its acid halide, (3) its mixed acid anhydride, (4) its acid amide, (5) its ester, (6) its acid azide or (7) its nitrile.

* * * * *